United States Patent [19]

Appelbaum et al.

[11] Patent Number: 4,818,696

[45] Date of Patent: Apr. 4, 1989

[54] RHIZOBIUM JAPONICUM SYMBIOSIS GENE TRANSFER

[75] Inventors: Edward R. Appelbaum, Madison; Thomas J. McLoughlin, Monona, both of Wis.; Michael P. O'Connell, Bielefeld, Fed. Rep. of Germany

[73] Assignee: Lubrizol Genetics, Inc., Wickliffe, Ohio

[21] Appl. No.: 616,950

[22] Filed: Jun. 1, 1984

[51] Int. Cl.$^4$ .................. C12N 15/00; C12N 1/20; C12R 1/41; C07H 21/00

[52] U.S. Cl. .................. 435/172.3; 435/172.2; 435/320; 435/878; 435/252.2; 935/29; 935/64; 935/72; 800/1; 536/27; 47/57.6

[58] Field of Search ............ 435/172.2, 172.3, 253, 435/317, 878, 320; 536/27; 47/57.6; 935/27, 29, 64, 72, 30; 800/1

[56] References Cited

U.S. PATENT DOCUMENTS 4,517,008   5/1985   Strobel ........................ 435/172.3

OTHER PUBLICATIONS

Long, S., et al, *Nature*, vol. 298, pp. 485–488, 1982.
Hennecke, H., *Nature*, vol. 291, pp. 354–355, 1981.
Ruukun, G. et al., *Cell*, vol. 29, pp. 551–559, 1982.
Brewin, N. J. et al, *J. Gen. Microbiology*, vol. 120, pp. 413–420, 1980.
Engwall, K. et al, Abstracts, ASM, Annual Mtg., p. 101, Mar., 1984.
Appelbaum, E. R. et al, in *Adv. Nitrogen Fixation Res.*, (Eds. Veeger C. & Newton, W. E.), p. 670 (1983).
Yelton, M. M. et al, *J. Gen. Micriol.*, vol. 129, pp. 1537–1547, 1983.
Masterson, R., et al., *J. Bacteriol.*, vol. 152, No. 2, pp. 928–931, Nov., 1982.
Kondorosi, A. et al., *Mol. Gen. Genet.*, vol. 188, pp. 433–439, 1982.
Simon, R. et al., in *Molec. Genet. Bacteria-Plant Interactions*, (Ed. Pohler, A), pp. 98–106, 1983.
Simon, R. et al, *Mol. Gen. Genet.*, vol. 196, pp. 413–420, 1984 (Sep.).
Appelbaum, E. et al, *J. Bacteriol.*, vol. 163, No. 1, pp. 385–388, Jul., 1985.
Masterson, R. et al, Abstracts, ASM Annual Mtg. p. 96, (Mar. 1984).
Engwall, K. et al, *Adv. Nitrogen Fixation Res.*, (Eds. Veeger C. V. Newton, W. E.) p. 679, 1984.

*Primary Examiner*—Jayme A. Huleatt
*Attorney, Agent, or Firm*—Greenlee and Associates

[57] ABSTRACT

A symbiosis plasmid from a fast-growing *Rhizobium japonicum* donor strain can be transferred to Rhizobium recipient strains, the recipient strains being previously incapable of forming an effective symbiotic relationship with plants of certain Glycine (e.g. soybean) varieties. The recipient strains harboring the symbiosis plasmid will form effective symbioses with soybean plants of said certain varieties, the transferred symbiosis plasmid conferring the host range or specificity of the donor strain on the recipient strains. Methods, strains, and plasmids useful for practice of this invention are also provided.

34 Claims, 1 Drawing Sheet

RHIZOBIUM JAPONICUM SYMBIOSIS GENE TRANSFER

FIELD

The present invention is in the fields of biological nitrogen fixation and genetic engineering of rhizobia.

BACKGROUND

Rhizobium-legume symbiosis has been recently reviewed by D. P. S. Verma and S. Long (1983) Intnatl. Rev. Cytol. Suppl. 14:211-245. J. E. Beringer (1982) in *Proc. 8th N. Amer. Rhizobium Conf.*, eds.: K. W. Clark and J. H. G. Stephens, review transfer of symbiosis plasmids (pSym) between fast-growing species of Rhizobium. Fast-growing rhizobia (e.g. *R. leguminosarum, R. meliloti, R. phaseoli*, and *R. trifolii*) are classified within the family Rhizobiaceae. Following are representative examples of publications disclosing transfer of symbiosis plasmids and genes.

S. Higashi (1967) Gen. Appl. Microbiol. 13:391-403, transferred the ability to nodulate (i.e. Nod phenotype, or nod gene) clover from *R. trifolii* to *R. phaseoli* without artificially genetically marking the transferred pSym. A. W. B. Johnston et al. (1978) Nature 276:634-636, transferred a Tn5-marked conjugative plasmid that directed synthesis of a bacteriocin from a pea-nodulating *R. leguminosarum* into clover-nodulating *R. trifolii* and kidney bean-nodulating *R. phaseoli*. The resultant transconjugants were observed to gain the ability to form nodules on peas, though the ability to fix (i.e. Fix phenotype) nitrogen was not the same for all transconjugants. Conversely, P. J. J. Hooykaas et al. (1981) Nature 291:351-353, similarly transferred a Tn5-marked conjugative plasmid from *R. trifolii* to *R. leguminosarum*, resulting in effective nodulation on clover, and to *Agrobacterium tumefaciens* (a member of the family Rhizobiaceae), producing abaerrant, Fix− clover nodules. B. G. Rolfe et al. (1983) in *Molec. Genet. Bacteria-Plant Interactions*, ed: A. Pühler, pp. 188-203, report a *R. leguminoserum*-derived Sym plasmid that exchanged pea-specific functions for clover-specific functions by in vivo recombinational exchange of 60 kilobase pairs (kbp) of *R. trifolii* pSym DNA. The resultant transconjugants were Nod+ Fix+ on clover. J. W. Lamb et al. (1982) Mol. Gen. Genet. 186:449-452, found that a *R. phaseoli* plasmid could confer to *R. leguminosarum* the ability to nodulate and fix nitrogen on beans.

N. J. Brewin et al. (1980) J. Gen. Microbiol. 116:261-270, demonstrated that the plasmid of Johnston et al., supra, could complement nod− and fixation-defective (fix− gene) mutants of *R. leguminosarum* and restore strains to Nod+ and Fix+ phenotypes. N. J. Brewin et al. (1980) J. Gen. Microbiol. 120:413-420 showed that transfer of conjugative plasmids between different strains of *R. leguminosarum* can change the host-range specificity for effective symbiosis of the Rhizobia for different varieties of peas. G. Hombrecher et al. (1984) Mol. Gen. Genet. 194:293-298, found that the *R. leguminosarum* gene(s) determining which pea varieties are nodulated are located within a 5 kbp region of DNA. A. Kondorosi et al. (1983) in Pühluer, supra, pp. 56-63, have tentatively identified a particular nod gene determining host specificity in *R. meliloti*.

Z. Bánfalvi et al. (1983) Mol. Gen. Genet. 189:129-135, have made R-prime plasmids carrying symbiotic genes of *R. meliloti*. A. Kondorosi et al. (1982) Mol. Gen. Genet. 188:433-439, introduced a RP4 mobilization (mob) site into a *R. meliloti* pSym and in the presence of RP4 and related plasmids were able to transfer the resultant plasmid and Nod+ Fix+ phenotypes into other rhizobial stains. J. A. Downie et al. (1983) Mol. Gen. Genet. 190:359-365, and S. R. Long et al. (1982) Nature 298:485-488, have made recombinant DNA plasmids in vitro which carry nod genes of *R. leguminosarum* and *R. meliloti*, respectively, that are capable of complementing nod− mutants. The *R. leguminosarum* genes were located on a 10 kbp DNA region that, when transferred into a *R. phaseoli* strain cured of its endogenous pSym, caused nodulation of peas. E. Kondorosi et al. (1984) Mol. Gen. Genet. 193:445-452, have identified nod and fix gene-containing clones in a cosmid library of *R. meliloti*. Hombrecher et al., supra. have identified nod gene-carrying cosmids derived from *R. leguminosarum*.

Replacement of absent (e.g. deleted) or defective (e.g. mutated) genes is a technique well known in the art of microbiology. Replacement of nod and fix is described in a number of publications, including, but not limited to, the following above cited works: Johnston et al., Hooykaas et al., Rolfe et al., Lamb et al., Brewin et al., J. Gen. Microbiol. 116:261-270 and 120:413-420, Hombrecher et al. A. Kondorosi et al. (1983) and (1982), Bánfalvi et al., Downie et al., Long et al., and E. Kondorosi et al. Replacement of a gene generally entails introduction of a plasmid carrying a functional copy of that gene into a cell. Often the cell is previously cured of an endogenous plasmid carrying that gene.

J. O. Berry and A. G. Atherly (1982) in *Proc. 8th N. Amer. Rhizobium Conf.*, eds: K. W. Clark and J. H. G. Stephens, pp. 115-128, and (1984) J. Bacteriol. 157:218-224, introduced plasmids into slow-growing strains of *R. japonicum* but did not demonstrate conjugal transfer of Glycine-active symbiotic genes between bacterial strains. *R. lupini*, various Rhizobium "species", and most strains of *R. japonicum* are slow-growers. K. S. Engwall and A. G. Atherly (March 1984) Abstracts, Amer. Soc. Microbiol. Annual Meeting, St. Louis, MO, p. 111, and K. S. Engwall et al. (1984) in *Adv. Nitroqen Fixation Res.*, eds: C. Veeger and W. E. Newton, p. 679, have presented data indicating that *Agrobacterium tumefaciens* cells containing plasmid from a fast-growing *R. japonicum* strain will form associations with soybean roots, the roots then forming "bumps" reminiscent of root nodules (i.e. aberrant nodules) but lacking bacteroid release and ineffective in nitrogen fixation. A large plasmid present in USDA191, designated herein as pSym191, had DNA sequences homologous to nitrogen fixation (nif) genes of *Klebsiella pneumoniae* (E. R. Appelbaum et al., in Veeger and Newton, supra, pg. 670) and *R. meliloti* (R. V. Masterson et al. (1982) J. Bacteriol. 152:928-931) as determined by nucleic acid cross-hybridization. It is believed that the present invention is the first disclosure of transfer between different Rhizobium strains of genes determining host specificity of the symbiosis of rhizobia with any members of the genus Glycine and in particular soybean (Glycine max L.) varieties.

Plasmid vectors that can be transferred from *E. coli* to Rhizobium, that are maintainable in *E. coli* but not in Rhizobium, and that carry a mob-bearing transposon capable of mobilizing DNA transfer among a wide range of gram-negative bacteria have been disclosed by R. Simon et al. (1983) in *Molec. Genet. Bacteria-Plant Interactions*, ed. A. Pühler, pp. 98-106. Such vectors are of a class known as "suicide vectors". No cells can be stably transformed by autonomous suicide vector; the vector, having a replicon not capable of being maintained in rhizobia, "commits suicide" after introduction into a rhizobial cell. After cells have been transformed by a suicide vector, the only cells isolated after selection for a transposon-carried genetic marker will be those having a copy of the transposon incorporated into a replicon-containing DNA molecule already present and stably maintained in the cell.

The combination of rhizobial cells with a carrier material thereby forming an inoculant composition or a seed coating composition, and additionally with a binder material thereby forming a seed coating composition, is a well understood technology. The use of such compositions is also well understood.

SUMMARY

Prior art methods have been unable to change the host range of Rhizobium strains for symbiosis with plants of the genus Glycine (e.g. soybeans), i.e. to enable a strain to form a symbiosis with (i.e. to nodulate on and fix nitrogen for) Glycine plants previously not within that strain's host range. The plants outside the strain's original host range might be any Glycine plants or a particular variety of Glycine plants. It is therefore, an object of this invention to provide a means for extending or changing the host range or symbiotic specificity of rhizobial cells for soybean plants and plants of closely related species. Other objects and advantages will become evident from the following description.

We have discovered that DNA determining host range of symbiosis can be transferred from one *R. japonicum* strain to other Rhizobium strains. Before this discovery, it was not known whether genetic material sufficient for Glycine-specific symbiotic nitrogen fixation could be isolated on a single DNA molecule which would be functional when transferred into a different Rhizobium strain, itself not capable of forming effective nodules on Glycine max or on a particular variety of soybean. We believe the results presented herein to be the first disclosure of the transfer of a nitrogen-fixing, Glycine-nodulating phenotype between two strains of Rhizobium. These results were demonstrated by inserting a transposon carrying a mob-site (a DNA sequence capable of being mobilized for conjugal transfer) and a drug resistance gene into a donor cell's *R. japonicum* plasmid, mobilizing the modified plasmid, conjugally transferring it into a recipient cells, selecting a transformed cell, and demonstrating biologically a changed specificity on Glycine plants for nodulation and symbiotic nitrogen fixation. We believe our results to be the first demonstration that a *R. japonicum* plasmid can be a fully functional pSym carrying nif and nod genes needed to confer on nif− or nod− Rhizobium strains the ability to symbiotically fix nitrogen in Glycine root nodules. We also believe our results to be the first demonstration that the selectivity of an *R. japonicum* strain for effective symbiosis with particular varieties of soybeans (i.e. the host-range or specificity) can be changed. The invention disclosed herein therefore provides methods and materials, such as plasmids and bacterial strains, suitable for effecting *Rhizobium japonicum* symbiosis gene transfer.

It is an object of the present invention to produce a recombinant DNA molecule comprising a Glycine-specific sum gene and a t-vector DNA. A further object is that this DNA additionally comprises a mob-site, and in particular mob-site derived from RP4 or a factor that cross-mobilizes therewith. A further object is that transposon sequesnces flank the mob-site. Preferably, the mob-site is derived from RP4 or a factor that cross-mobilizes therewith, the transposon sequences are derived from Tn5, the prefered Tn5/mob-site combination being donated to the DNA by pSUP5011. A further object is that this DNA be a plasmid. A further object is that the Glycine-specific sym gene has a phenotype of nodulating genetically improved cultivars of Glycine max L. Preferably, the Glycine-specific sym gene is from pSym191. Also preferably a mob-site is inserted into pSym191.

Another object of this invention is to provive an improved Rhizobium bacterium capable of effective Glycine-specific symbiotic nitrogen fixation containing a recombinant DNA molecule, the DNA comprising a Glycine-specific sym gene and a t-vector DNA. Preferably, this bacterium is cured of an endogenous sym gene-carrying plasmid. A further object is that the DNA comprising a Glycine-specific sym gene obtained from a donor strain, wherein the resultant strain containing the sym gene/t-vector combination is more competitive than the donor strain. Preferably, the bacterium is of a fast-growing strain of Rhizobium, as is exemplified herein by bacteria derived from USDA191, USDA257, NGR234, *R. meliloti* 2011, or *R. leguminosarum* 6015. These exemplified embodiments include *R. meliloti* (Sm$^r$) (pSym191::Tn5-mob)(RP4-4), a Nod+ Fix+ isolate of USDA257 (pSym257::191::Tn5-mob)(RP4-4), ANU265 (pSym191::Tn5-mob)(RP4-4), *R. leguminosarum* 6015 (pSym191::Tn5-mob)(RP4-4), USDA191 (pSym191::Tn5-mob), USDA191-C3 (pSym257::191::Tn5-mob)(RP4-4), USDA191-C3 (pSym191::Tn5-mob)(RP4-4), and USDA191 (pSym191::Tn5-mob). Further objects are to produce an inoculant composition comprising a carrier material and the improved Rhizobium bacterium and to produce a seed of the genus Glycine coated or otherwise physically associated with material comprising the inoculant composition.

Another object of this invention is to provide a method for the production of an improved Rhizobium strain which comprises the step of (a) introducing a Glycine-specific sym gene from a donor Rhizobium strain into a recipient Rhizobium strain, whereby the host range of effective symbiosis of the recipient strain with plants of the genus Glycine is changed. Preferably the donor and recipient Rhizobium strains are fast-growing *R. japonicum* strains, as is exemplified herein with the donor strain being USDA191 and the recipient strains being or being derived from USDA257, NGR234, *R. meliloti* 2011, or *R. leguminosarum* 6015. A further object is to provide a method which comprises the step of (b) mating the donor strain with the recipient strain, whereby the Glycine-specific sym gene is introduced from the donor into the recipient. A further object is that this method further comprises before execution of step (b) the step of (c) inserting a mob-site into a DNA molecule comprising the Glycine-specific sym gene, thereby genetically linking the mol-site and the Glycine-specific sym gene. Preferably in this method the mob-site is derived from RP4 or a factor cross-moblilizes therewith and the mob-site is flanked by transposon sequences. A further object is that this method further comprises before execution of step (c) the step (d) introducing into the donor cell a suicide vector comprising the transposon/mob-site combination. Preferably the suicide vector is pSUP5011 or a derivative thereof. A further object is that this method further comprises after execution of step (a) the step(s) of (e) selecting Glycine-specific sym gene transformed recipient cells by growth on one or more antibiotics, and/or (f) selecting Glycine-specific sym gene transformed recipient cells by identifying and recovering those presumptive transformed recipient cells which symbiotically interact with Glycine root tissue. A further object is that this method further comprises after the execution of step (c) the step of (g) mobilizing the DNA molecule of step (c) for conjugal transfer. Preferably the DNA of step (c) is mobilized by introducing into the donor cell RP4, RP4-4, a factor that cross-mobilizes therewith or a derivative thereof. A further object is that this method further comprises before execution of step (a) the step of (h) curing the recipient strain of an endogenous pSym. In many embodiments, a DNA molecule comprising the Glycine-specific sym gene genetically recombines in vivo with an endogenous DNA molecule comprising a replicon, thereby genetically linking the Glycine-specific sym gene with the endogenous replicon.

Another object of this invention is to provide an improved Rhizobium bacterium capable of Glycine-specific symbiotic nitrogen fixation produced according to a method comprising the step of introducing a Glycine-specific sym gene from a donor Rhizobium strain into a recipient Rhizobium strain. Preferably, the donor and recipient strains are fast-growing Rhizobium strains, as exemplified herein with USDA191, NGR234, *R. meliloti* 2011, or *R. leguminosarum* 6015, or derivatives thereof. A further object is that the improved bacterial strain be more competitive than the donor strain. Exemplified bacterial strains include *R. meliloti* (Sm$^r$) (pSym191::Tn5-mob)(RP4-4), a Nod+ Fix+ isolate of USDA257 (pSym257::191::Tn5-mob)(RF4-4), ANU265 (pSym191::Tn5-mob)(RP4-4), *R. leguminosarum* 6015 (pSym191::Tn5-mob)(RP4-4), USDA191 (pSym191::Tn5-mob), USDA191-C3 (pSym257::191::Tn5-mob)(RP4-4), USDA191-C3 (pSym191::Tn5-mob)(RP4-4), and USDA191 (pSym191::Tn5-mob). Futher objects include providing an inoculant composition comprising a carrier material and the improved bacterium and providing a seed of the genus Glycine coated or otherwise physically associated with that inoculant composition.

The present invention is useful for the production of improved rhizobial strains, and inocula for symbiotic nitrogen fixation on Glycine plants, such strains and inocula having traits otherwise not combined in other soybean-nodulating rhizobia. Such traits may include, but are not limited to, nodulation on other plant species, more efficient nitrogen fixation (e.g. improved nitrogenase genes, hydrogen uptake (hup) genes, etc.), improved seed coating properties, increased competitiveness, improved growth properties in industrial fermenters, specific identifying characteristic that are useful towards protection of proprietary rights, and the like. Should a strain have a number of desired phenotypes but not form a symbiosis on a particular soybean or Glycine variety, the present invention enables one to change the host range of that strain; prior to the present invention each of the non-host range phenotypes would have to be moved into a Glycine-nodulating and fixing strain.

DETAILED DESCRIPTION OF THE INVENTION

Figure 1:
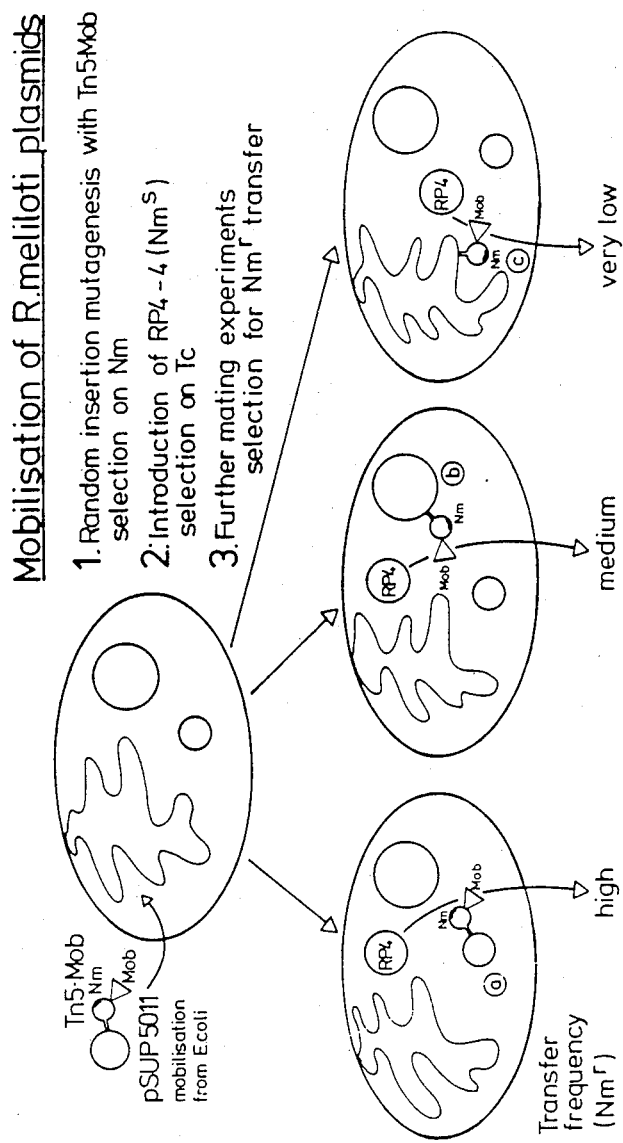
FIG. 1 is a schematic diagram describing the strategy used to move pSym191 from *R. japonicum* USDA191 to other Rhizobium strains. The three numbered steps describe operations used, and the three lettered schemes diagram possible outcomes of the manipulations.

The following definitions are provided in order to remove ambiguities to the intent or scope of their usage in the specification and claims.

Replicon: A fundamental unit of replication comprising all the genetic elements sufficient to confer autonomous replication in a bacterial cell, together with the DNA whose replication is controlled thereby. The bacterial chromosome, plasmids, and phage DNAs are examples of replicons existing in a bacterial cell. Individual replicons differ in the extent to which they are functional in different host cell species. Replicons such as RP4 are able to replicate in a wide range of gram-negative bacterial hosts.

Mob-site: A genetic locus necessary for mobilization of a plasmid transferable by bacterial conjugation. The mob-site (mobilization site) is believed to include oriT, the site of origin of transfer replication. The mechanism of DNA transfer by bacterial conjugation includes a replication of the plasmid in which a break is introduced into one strand of duplex plasmid DNA. DNA replication then commences at the site of the break followed by transfer of the cut strand to the recipient cell. The mob-site is considered to be the site of action of certain trans-acting functions coded by tra (transfer) genes. The existence of a mob-site is a necessary condition for transfer; however, the tra functions must also be provided. Since the latter act in trans the genes which code for them may be located elsewhere in the cell; for example, on another replicon. Tra functions and mob-sites also differ with respect to host range. For example, the tra functions and mob-site of the F factors are limited in function to conjugal transfers between members of the *E. coli* group. By contrast, the tra functions and mob-site of the plasmid RP4 permit its conjugal transfer over an exceedingly wide range of gram-negative organisms.

T-vector (from transfer vector): Refers herein to a nonrhizobial DNA molecule or DNA segment capable of facilitating transfer of rhizobial DNAs from one strain of Rhizobium to another, provided that the t-vector DNA and the rhizobial DNA being transferred are genetically linked to each other. Examples of t-vectors include, but are not limited to, replicons (e.g. plasmids) capable of independent replication in rhizobial cells, DNA segments (e.g. transposons) having mob-sites (i.e. a genetic locus necessary for mobilization of a plasmid transferable by bacterial conjugation), transposons bearing selectable markers, rhizobial viruses, and the like. A t-vector will often have an origin of DNA replication capable of maintaining genetically-linked DNA in a host cell, for example an RP4 replicon, a pBR325 replicon, or an origin of transfer replication, e.g. oriT.

Glycine-specific sym gene: Refers herein to any rhizobial gene that when transferred from a donor strain to at least one recipient strain is sufficient to change the host range of effective symbiosis of the recipient strain with plants of the genus Glycine (e.g. soybeans). The untransformed recipient may be a strain or derivative of a strain that either does not form a symbiosis with Glycine plants or forms a symbiosis with a first particular set of Glycine varieties, while the Glycine-specific sym gene-transformed recipient will form a symbiosis with a second particular set of Glycine varieties. The first and second particular sets of Glycine varieties must be different from each other, though one set may include all of the members of the other set. Indeed one of the two sets may include all Glycine plant varieties. As used in the term Glycine-specific sym gene, the term gene is defined as a heritable trait; a Glycine-specific sym gene may be made up of one or more genetic elements (e.g. cistrons, operons, etc.) and such elements may or may not be genetically linked to each other. Glycine-specific sym-gene is abbreviated herein as Gss-gene.

Underlying the present invention is the discovery that the ability to nodulate plants of the genus Glycine the host-specificity of nodulation, and the ability to fix nitrogen can be conferred on cells of a recipient strain when a symbiosis plasmid from a R. japonicum donor strain is transferred to other strains of Rhizobium. The fundamental principles of the present invention involve transfer a Glycine-specific sym gene between rhizobial strains and are not limited to the specific embodiments disclosed herein.

Extension or changes of Glycine-specific host range properties of rhizobial cells by means of obtaining a Gss-gene from a donor R. japonicum strain and then introducing the sym gene into a recipient Rhizobium strain combines specific teachings of the present disclosure with a variety of techniques, expedients, and discoveries known in the art. In most instances, alternative expedients exist for each stage of the overall process. The choice of expedients depends on such variables such as the targeted host plant varieties, the donor strain, the recipient strain, the Gss-gene transferred between strains, the means for transferring the Gss-gene between strains (i.e. the means for obtaining from one strain and introducing into another), DNA molecules (e.g. vectors, plasmids, transposons, or molecules to which Gss-gene DNA may be genetically linked), and the like. Many variants are possible for intermediates and intermediate process steps.

In the practice of the present invention, one ordinarily must first obtain a DNA molecule containing a Gss-gene, the gene having a phenotype of the desired host range specificity properties. A number of expedients are possible. In the preferred embodiments, the Gss-gene is obtained from a fast-growing *R. japonicum* strain; however, the present invention is not limited to fast-growing strains as donors. Although a Gss-gene is obtained from a plasmid in the preferred embodiments, it will be understood that a chromosomally-located Gss-gene can be isolated from a donor strain and transferred to a recipient. It also will be understood that should the Gss-gene be made up of unlinked genetic elements (e.g. two operons, each on a different plasmid) all of those elements must be transferred to the recipient strain. The size range of the rhizobial DNA obtained forms a wide spectrum, ranging from DNA carrying the Gss-gene of interest with no extraneous genes to large DNAs, e.g. pSyms, carrying many genes not involved in host range specificity.

One means for transfer of an entire pSym involves the insertion of a t-vector carrying a mob-site into a pSym, thereby genetically linking the mob-site and the Gss-gene. One means for insertion of a mob-site is by transposition of a mob-site-bearing transposon, preferably carried by a suicide vector, into the pSym, as is exemplified herein. Other means for insertion of a mob-site-bearing t-vector include use of a shuttle vector (G. B. Ruvkin and F. M. Ausubel (1981) Nature 289:85–88) to transfer a pSym DNA segment, having a mob-site inserted within the pSym DNA by in vitro recombinant DNA techniques well known to those of ordinary skill in the art of DNA splicing, into a pSym by double-homologus recombination (i.e. marker exchange), one recombinational event occurring on each side of the mob-site. One common system involves the use of pRK290-based vectors mobilized by pRK2013 (G. Ditta et al. (1980) Proc. Natl. Acad. Sci. USA 77:7347–7357) and excluded by pPHIJI (P. R. H1rsh (1978) Thesis, Univ. E. Anglia). Other shuttle vector systems have been disclosed by R. Simon et al. (1983) in Pühler, supra. Suicide vector systems, having replicons not functional in rhizobia, have been disclosed by R. Simon et al. (1983) Biotechnol. 1:784–791, and R. Simon et al. (1983) in Pühler, supra. Formation and transfer of R-prime plasmids analogous to those described by Bánfalvi et al., supra, provides an alternate means for transfer of an entire pSym. Transposon marked pSyms may be transferred conjugally, using methods analogous to those described by Johnston et al., supra for a *R. leguminosarum* pSym.

A self-transmissible pSym may be transferred between two Rhizobium strains without the plasmid itself being marked with a transposon-carried selectable marker or otherwise being modified by addition of extraneous DNA. Analogous manipulations have been exemplified by Higashi, supra, in a *R. trifolii* to *R. phaseoli* transfer. A prerequisite for this transfer is a means for selection against the donor strain. Donor and recipient cells are mated together followed by elimination of donor cells. Some of the remaining recipient cells will contain a donor-derived pSym. The cells may be screened or selected for by inoculation of the mixture or isolated clones upon a Glycine variety with which the untransformed recipient strain is unable to form an effective (i.e. Nod+ and Fix+) symbiosis. Transformed recipient strains may be recovered from root nodule bacteroids by methods well known in the art.

Alternatively, a pSym may itself carry a drug resistance marker. R. Simon et al. (1983) Biotechnol. 1:784–791, and R. Simon et al. (1983) in Clark and Stephens, supra, pp. 67–89, provide suitable means for marking pSyms with transposons. Marking a pSym with a drug-resistance marker, e.g. Tn5, may be advantageous, as will be understood by those of ordinary skill in the art of bacterial genetics, though one must not choose a clone having a Gss-gene inactivated by the transposon. It should also be noted that during transfers of unmodified pSyms, the steps of obtaining a Gss-gene and transferring the Gss-gene into recipient cells are executed simultaneously.

At the other end of the DNA size spectrum is the transfer of a small number of genes--perhaps just the Gss-gene--to the recipient strain. The Gss-gene may be cloned by recombinant DNA technology. Cells harboring plasmids carrying a Gss-gene may be identified by hybridization to probes including probes for known Gss-genes. Alternatively, the recombinant molecules can be introduced into rhizobia that are $Nod^-$ on a particular cultivar which are then selected for a $Nod^+$ phenotype using a strategy analogous to that described above for biological selection of self-transferable pSym-containing cells.

After a Gss-gene is obtained, the sym gene is introduced into a recipient Rhizobium strain. A number of expedients are possible for this step, the particular expedient chosen being influenced by the means for obtaining the Gss-gene.

Several expedients exist if a relatively small DNA segment is to be introduced into a recipient strain. The t-vector/Gss-gene combination may be introduced into the recipient cell by mating if the t-vector is mobilizable, by direct transformation, or by infection if the t-vector is a transducing phage or cosmid. The Gss-gene may by independently maintained in the cell if linked to a vector having a replicon functional in Rhizobium. Alternatively, the Gss-gene-bearing DNA may be introduced into an endogenous DNA molecule having its own replicon by means of homologous recombination with Gss-gene-linked homology to a cellular sequence, nonhomologous recombination, or transposition of a transposon into which the Gss-gene had been previously inserted.

Large DNA molecules, especially complete symbiosis plasmids, are most conveniently and efficiently introduced into a recipient strain by conjugation or mating. As described elsewhere herein, pSyms may be conjugally transferred without introduction of an exogenous mob-site. However, the preferred embodiment entails introduction of an exogenous mob-site genetically linked to a selectable marker (herein an Nm antibiotic resistance gene which confers resistance to neomycin and its analogs e.g. kanamycin and G418). (Note that pSym191 is reported by Engwall et al., supra, to be not self-transmissible.) The mob-site and the marker are preferably of a Tn5-derived transposon introduced into the donor cell on a suicide plasmid; only cells having the transposon linked to replicon previously present are resistant to the selecting drug. A mobilizing plasmid carrying trans-acting tra (transfer) genes that mobilize the mob-site inserted in the pSym is then introduced into the donor cell. The pSym/mob-site combination is thereby mobilized and can be transferred into a recipient cell by mating. Cells containing the pSym/mob combination are selected by their drug-resistant phenotype and can be shown to have gained the ability to nodulate previously unnodulatable Glycine varieties.

In the preferred embodiment the mobilizing plasmid was cotransferred along with the pSym/mob combination. The mobilizing plasmid does not affect symbiotic properties and, in any case, it may be eliminated (or "cured") by techniques known in the art, e.g. growth of cells at elevated temperatures, growth in the absence of selective pressure, treatment with detergents, etc. A pSym/mob combination may integrate into and become genetically linked with an endogenous pSym or another endogenous relicon. A transferred Gss-gene may interact with one or more endogenous sym genes, thereby creating new phenotypes. This may be prevented by curing the recipient strain of endogenous pSyms or by careful selection or screening of the donated Gss-gene.

After introduction of a foreign Gss-gene-carrying DNA molecule into a recipient strain, the resultant strain is tested for altered symbiotic properties. As described above, these properties may be used to select Gss-gene-transformed cells from untransformed cells of the recipient strain. In the preferred embodiment, the Gss-gene is introduced into fast-growing Rhizobium strains; however, the present invention is not limited to fast-growing strains as recipients.

A recipient strain transformed to be capable of Glycine-specific symbiosis may be grown in bulk quantities in industrial fermenters as is understood in the art. After growth the cells may be stored and distributed as liquid solution (e.g. in the spent culture media), as a freeze-dried powder, as a frozen paste produced by centrifugation of the culture, etc. Rhizobial powders or pastes may be resuspended in water near the site of field application. Rhizobial solutions in the form of culture solutions or derived from paste or power may be introduced directly to a soybean field by application into the furrow at planting time. Alternatively, the rhizobia may be combined with a carrier and possibly with other agronomically useful materials. Such agronomically useful materials include plant nutrients, other soil microorganisms, pesticides, herbicides, substances beneficial to rhizobial cells (e.g. polyvinyl-pyrolidone), and the like. Carrier materials include clays (e.g. bentonite or kaolin), peat, powdered charcoal, ground coal, vegetable (e.g. peanut) oil, gels (e.g. agar, alginate, gum arabic), cellulosic materials (e.g. ground coconut husks (copra), paper pulp, wood pulp, ground corn cobs, and the like), and so forth. Some carrier material/Rhizobium compositions must additionally include a binder material. Binder materials include sugar solutions (e.g. molasses), beer, caseinate salts, carboxymethylcellulose, the above mentioned gels, oil, controlled amounts of water, and other sticky materials. A solid Rhizobium/carrier combination in granular form may be applied in furrow as is done with liquid application. Alternatively, a Rhizobium/carrier combination may be used to coat a soybean seed. Considerations in the combination of further expedients and those expedients mentioned above are understood in the art.

EXAMPLES

The following Examples utilize many techniques well known and accessible to those skilled in the arts of molecular and bacterial genetics and manipulation of mobilizable plasmids and Rhizobia: other methods are described in one or more of the cited references if not described in detail herein. Reagents and materials were obtained from commercial sources. Reagents, buffers, media, and culture conditions are known to those in the art. Rhizobia were usually grown on TY medium (5 g/l tryptone, 3 g/l yeast extract, 7 mM CaCl$_3$) and stored on YM medium (0.5 g/l K$_2$HPO$_4$, 0.2 g/l MgSO$_4$.7-H$_2$O, 1 g/l yeast extract, 0.2 NaCl, 4.88 mg/l FeCl$_3$, 10 g/l mannitol); both TY and YM may be solidified by addition of 15 g/l agar. Reference works containing such standard techniques include J. H. Miller (1972) *Experiments in Molecular Genetics*, R. Davis et al. (1980) *Advanced Bacterial Genetics*, R. F. Schleif and P. C. Wensink (1982) *Practical Methods in Molecular Biology*.

Plasmids are prefaced with a "p", e.g. pSym191 is the USDA191 harbored plasmid carrying symbiosis genes. A strain designations followed parenthetically by a plasmid name, e.g. *E. coli* SM10 (pSUP5011), indicates that the strain is harboring a plasmid not present in the type strain. Drug-resistant mutants are also indicated parenthetically, e.g. USDA191 (Rif$^r$) is a rifampicin-resistant derivative of USDA191. Antibiotic abbreviations (and concentrations commonly used, unless otherwise specified) were as follows: Sm (about 200 mg/l) is streptomycin; Spc (250 mg/l) is spectinomycom; Nm (100 mg/l) is neomycin (kanamycin, or Kn (50 mg/l, is an analog thereof and may be substituted for Nm with appropriate modifications well understood in the art);

and Tc (5 mg/l) is tetracycline; Rif (50 mg/l) is rifampicin. Strains listed in Table 1 were deposited with the U.S. Department of Agriculture, Northern Regional Research Center, 1815 N. Universtiy Street, Peoria, Ill. 61604, USA, before the filing of the present application.

As exemplified herein, the pSym of a strain completent to form an effective nitrogen-fixing symbiosis on genetically improved (e.g. "Williams") (M. M. Yelton et al. (1983) J. Gen. Microbiol. 129:1538–1547, T. J. McLoughlin et al. (1983) Program, 9th N. Amer. Rhizobium Conf.) and unimproved (e.g. wild; e.g. "Peking") soybean plants, USDA191 (H. H. Keyser et al. (1982) Science 215:1631–1632), was transferred to a strain unable to effectively nodulate soybeans, ANU265, derived from ANU240, which we have found to be Nod$^{abberent}$ and to not form an effective symbiosis with soybeans. ANU265 is a plasmid-cured Spc$^r$ derivative of ANU240, which is a Sm$^r$ NGR234 derivative (N. A. Morrison et al. (1983) J. Bacteriol. 153:527–531). NGR234 is a broad host range, fast-growing Rhizobium strain reported by M. J. Trinick (1980) J. Appl. Bacteriol. 49:39–53. pSym191, the pSym of USDA191, was also transferred to a fast-growing R. japonicum strain able to form a symbiosis with Peking but unable to form an effective symbiosis with Williams, USDA257 (obtained from H. H. Keyser, U.S. Department of Agriculture, Agricultural Research Service, Cell Culture and Nitrogen Fixation Laboratory, Beltsville, MD 20705). Mobilization of pSym191 was carried out in three stages, each of which corresponds to an Example. Stage 1 was the transfer of pSUP5011, a Tn5-mob-carrying suicide vector, into R. japonicum USDA191 and selection of USDA191 recipients carrying the transposon. Stage 2 included introduction of a resultant pSym191::Tn5-mob and RP4-4 into R. meliloti. Stage 3 included mobilization of pSym191::Tn5mob, conjugal transfer thereof to USDA257, ANU265, and R. leguminosarum. and selection and characterization of recipient cells harboring pSym191::Tn5-mob sequences. Example 4 describes the biological activity of the Gss-gene in various rhizobial strains.

EXAMPLE 1

Introduction of Tn5-mob into pSym191

Mutagenesis of pSym191 is shown diagrammatically in FIG. 1 as step 1. E. coli SM10 (R. Simon et al. (1983) Biotechnol. 1:784–791) harboring pSUP5011 (R. Simon et al., in Pühluer, supra) (donor) was mated with USDA191 (Rif$^r$) (recipient) on nitrocellulose membrane filters, a technique well known in the art. S17-1 carries trans-acting mobilizing functions on its chromosome. The frequency of transconjugants resistant to 60 mg/l Nm and 100 mg/l Rif was consistent with plasmid transfer followed by transposon transposition. Rif$^r$ Nm$^r$ USDA191 clones were picked and grown in non-selective medium.

EXAMPLE 2

Transfer to R. meliloti

The mobilization and transfer steps of the Rif$^r$ Nm$^r$ USDA191 derivatives constructed in Example 1 were analogous to those shown diagrammatically as steps 2 and 3, scheme (b), of FIG. 1. The target replicon recipient strain was a Sm$^r$ derivative of R. meliloti 2011 (Sm$^r$) (obtained from J. Denarie, C.N.R.A., Versailles, France; see H. M. Meade and E. R. Signer (1977) Proc. Natl. Acad. Sci. USA 74:2076–2078). Twenty individual Rif$^r$ Nm$^r$ USDA191 isolates were used as donors on nitrocellulose filters to optimize the transfer conditions as follows: The mobilizing helper plasmid, RP4-4 was a Nm-sensitive derivative of RP4 (R. W. Hedges and A. E. Jacob (1974) Mol. Gen. Genet. 132:31-40, see also Simon et al., in Pühler, supra) and was harbored by E. coli MM294 (see G. B. Ruvkin and F. M. Ausubel (1981) Nature 289:85–88, also Davis et al., supra). Cultures of mobilizer (E. coli MM294 (RP4-4)) and donor were first mixed together, were incubated overnight on a nitrocellulose filter, were resuspended, and then were spotted together with recipient cells onto nitrocellulose filters and incubated on nonselective plates for several hours at 30° C. The filters subsequently transferred to plates containing a solidified selective medium containing 200 mg/l Sm and 100 mg/l Nm. Streptomycin killed donor cells, neomycin selected against those recipients in which the transposon was not linked to a stable replicon, and tetracycline can optionally be used to select for the presence of RP4-4. Three of the twenty Rif$^r$ Nm$^r$ USDA191 isolates produced R. meliloti transconjugants selectable on medium containing Nm and Sm. The three donor clones transferred neomycin resistance with a frequency consistent with transfer of a plasmid. The resulting strains were characterized by electrophoretic analysis of plasmid DNA. The strains were lysed essentially as described by T. Eckhardt (1978) Plasmid 1:584–588. The DNA was fractionated by electrophoresis in 0.8% (w/v) agarose gel in Tris-borate buffer for 3 hours at 120 V and stained with ethidium bromide. The DNA bands were visualized under ultraviolet light. Bands corresponding to RP4-4 and pSym191::Tn5-mob (pSym191 carrying the Tn5/mob combination of pSUP5011), having a molecular weight of approximately 200 megadaltons, were readily detected in one target replicon recipient 2011-derived cell previously identified as neomycin resistant. pSym191::Tn5-mob and RP4-4 were stably maintained in the 2011 (Sm$^r$) (pSym191::Tn5-mob)(RP4-4) transconjugant cells.

EXAMPLE 3

Transfer to recipient strains

The mobilization and transfer steps were a continuation of step 3, scheme (b), shown diagrammatically in FIG. 1. The donor cells were R. meliloti 2011 (Sm$^r$) (pSym191::Tn5-mob)(RP4-4). The target replicon recipients were R. leguminosarum 6015 (Spc$^r$) (6015 is Rif$^r$ and Sm$^r$, Johnston et al., supra), R. japonicum USDA257 (Spc$^r$), and ANU265 (which is Spc$^r$), which is derived from the broad host range Rhizobium strain NGR234. The matings were performed as described above on nitrocellulose filters to optimize the transfer conditions. Transconjugants of strains 6015 (Spc$^r$), 257, and 265 were respectively selected on medium containing 50 mg/l Spc and 50 mg/l Rif and 60 mg/l Nm, Spc and Kan, and Spc and Kan. The R. meliloti donor transferred neomycin resistance with a frequency consistent with transfer of a plasmid. The resulting strains were characterized by analysis of the plasmid DNA by electrophoresis. The strains were lysed essentially as described by T. Eckhardt (1978) Plasmid 1 584–588. The DNA was fractionated by electrophoresis in 0.8% (w/v) agarose gel in Tris-borate buffer for 3 hours at 120V and stained with ethidium bromide. The DNA bands were visualized under ultraviolet light. A band corresponding to pSym191::Tn5-mob was readily detected in the target replicon recipient ANU265-derived cells previously identified as neomycin resistant. pSym191::Tn5-mob was stably maintained in the ANU265 (pSym191::Tn5-mob)(RP4-4) transconjugant cells. Bands corresponding to a plasmid formed during recombinational events between pSym257 and pSym191::Tn5-mob-- comprising elements of both Sym plasmids, were detected in USDA257-derived transconjugates and are herein designated pSym257::191::Tn5-mob.

A USDA257 (pSym257::191::Tn5-mob)(RP4-4) isolate that was Fix+ on Williams was mated with USDA191-C3, a plasmid-cured Fix- Nod- Sm$^r$ derivative of USDA191. Transconjugants resistant to Tc, Sm, and Kn were found to contain RP4-4 and pSym257::191::Tn5-mob. R. meliloti 2011 (Sm$^r$) (pSym191::Tn5-mob)(RP4-4) was also mated with USDA191-C3 (Spc$^r$). Transconjugates resistant to Tc, Sm, and Kan were found to contain RP4-4 and pSym191.:Tn5-mob.

EXAMPLE 4

Biological activity

ANU265 (pSym191::Tn5-mob)(RP4-4), USDA191-C3 (Spc$^r$) (pSym191::Tn5-mob)(RP4-4), USDA191-C3 (pSym257::191:Tn5-mob)(RP4-4), and various clones of USDA257 (pSym257 :191::Tn5-mob)(RP4-4) were tested for their abilities to nodulate various lines of Glycine max L. (soybeans), including the wild, genetically unimproved variety "Peking" and the genetically improved cultivar "Williams". The presence of pSym191 DNA was observed to be capable of conveying USDA191—s ability to nodulate and fix nitrogen (assayed biologically and by acetylene reduction) on Williams to strains otherwise Fix- on that host. Host specificity of these strains and their parental strains are summarized and compared in Table 2; "+" and "—" indicate Fix+ or Nod+ and Fix- or Nod-, respectively. "+/—" indicates that some resultant isolates are Fix+ and some are Fix-. In the "+/—" case, resultant isolates after cointegration of pSym257 and pSym191::Tn5-mob sometimes had a complete set of sym genes and were Fix+ while others had an incomplete set and were Fix-. "a" indicates that abberant nodules were formed. "+/a" indicates that Fix+ isolates were Nod+ and that Fix- isolates were Nod$^{abberant}$. Though both R. meliloti 2011 (Sm$^r$) (pSym191::Tn5-mob) and R. leguminosarum 6015 (pSym191::Tn5-mob)(RP4-4) formed occasional Fix- swellings, neither was unable to form effective, normal-appearing nodules when inoculated onto soybeans.

The results summarized in Table 2 demonstrate that Gss-gene-bearing DNA of pSym191 was sufficient to change the Glycine-specific host range of a rhizobial strain caused to contain that DNA. That the entire pSym191 is not needed to determine Glycine-specific symbiosis was demonstrated by the results with USDA257 (pSym257::191::Tn5-mob)(RP4-4); not all isolates had the same pSym191 DNA segments as demonstrated by Southern blots of restriction digests probed with a sym DNA, resulting in Williams in Fix+ Nod+ isolates having the USDA191 Gss-gene and in Fix- Nod$^{abberant}$ isolates lacking the USDA191 Gss-gene. That the Gss-gene is not sufficient in all recipient rhizobia to cause Glycine-specific effective symbiosis was demonstrated by the results with the R. meliloti and the R. leguminosarum derivatives, though the formation of abberant nodules indicated partial Gss-gene function. Introduction of pSym-derivatives into a strain that had lost the ability to form a symbiosis with soybean (USDA191-C3) and into a strain that had never been able to do so (ANU265) gave those strains a Sym+ phenotype on soybeans, thereby demonstrating Gss-gene function. Broadening the host specificity within the species Glycine max by introduction of pSym191 DNA into USDA257 demonstrated that adding Gss-gene-bearing DNA to an R. japonicum genome was sufficient to extend the host range of effective symbiosis with Glycine plants of the USDA257 recipient from one set of soybean varieties (Peking but not Williams) to another set (both Peking and Williams).

TABLE 1

| Deposited Strains | |
|---|---|
| E. coli SM10 | NRRL B-15481 |
| E. coli CSH52 (pSUP5011) | NRRL B-15495 |
| R. meliloti 2011 (Sm$^r$) (pSym191::Tn5-mob) (RP4-4) | NRRL B-15787 |

TABLE 2

| | Host Specificity | | | |
|---|---|---|---|---|
| | Fix | | Nod | |
| | Peking | Williams | Peking | Williams |
| fast-growing R. japonicum (formerly known as fast growing R. japonicum) USDA191 | + | + | + | + |
| C3 fast-growing R. japonicum USDA191 | — | — | — | — |
| C3 fast-growing R. japonicum USDA191 (Spc$^r$) (pSym191::Tn5-mob)(RP4-4) | + | + | + | + |
| C3 fast-growing R. japonicum USDA191 (pSym257::191::Tn5-mob)(RP4-4)* | + | + | + | + |
| 2011 R. melilati (Sm$^r$) | — | — | — | — |
| 2011 R. melilati (Sm$^r$)(pSym191::Tn5-mob)(RP4-4) | — | — | a | a |
| USDA257 fast-growing R. japonicum | + | — | + | — |
| USDA257 fast-growing R. japonicum (pSym257::191::Tn5-mob)(RP4-4) | + | +/— | + | +/a |
| ANU240 fast-growing R. japonicum | — | — | a | a |
| ANU265 fast-growing R. japonicum | — | — | — | — |
| ANU265 fast-growing R. japonicum (pSym191::Tn5-mob)(RP4-4) | + | + | + | + |
| 6015 R. leguminosarum | — | — | — | — |
| 6015 R. leguminosarum | — | — | a | a |

TABLE 2-continued

| | Host Specificity | | | |
|---|---|---|---|---|
| | Fix | | Nod | |
| | Peking | Williams | Peking | Williams |
| (pSym191::Tn5-mob)(RP4-4) | | | | |

*Derived from a USDA257 (pSym257::191::Tn5-mob)(RP4-4) isolate previously shown to be Fix+ Nod+ on both varieties, the pSym having an approximate molecular weight of 260 megadaltons and having DNA segments derived from both pSym191 and pSym257, as demonstrated by Southern blots, a method well understood in the art.

We claim:

1. A recombinant DNA molecule comprising a Glycine-specific sym gene having the ability to provide effective nitrogen fixation and nodulation to a Glycine-nodulating rhizobial strain in a Glycine max L. host with which said strain does not naturally form a symbiotic relationship, and a t-vector DNA.

2. A recombinant DNA molecule according to claim 1 additionally comprising a mob-site.

3. A recombinant DNA molecule according to claim 2, wherein the mob-site from RP4, or a DNA which can mobilize RP4, or a DNA which can be mobilized by RP4.

4. A recombinant DNA molecule according to claim 2, further comprising transposon sequences flanking the mob-site.

5. A recombinant DNA molecule according to claim 4, wherein the tranposon sequences are derived from Tn5.

6. A recombinant DNA molecule according to claim 5, the Tn5 transposon sequences and the mob-site flanked therein being donated to the DNA by pSUP5011.

7. A recombinant DNA molecule according to claim 1, wherein the recombinant DNA is a plasmid.

8. A recombinant DNA molecule according to claim 1, wherein the Glycine-specific sym gene is from pSym191.

9. A recombinant DNA molecule according to claim 8, wherein a mob-site is inserted into pSym191.

10. A Rhizobium bacterium capable of effective Glycine-specific symbiotic nitrogen fixation containing a recombinant DNA molecule, the DNA comprising a Glycine-specific sym gene having the ability to provide effective nitrogen fixation and nodulation to a Glycine-nodulating rhizobial strain in a Glycine max L. host with which said strain does not naturally form a symbiotic relationship, with a t-vector DNA.

11. A bacterium according to claim 10, wherein the bacterium has been cured of an endogenous sym gene-carrying plasmid.

12. A bacterium according to claim 10, which is more competitive than a donor Rhizobium strain from which the Glycine-specific sym gene had been obtained.

13. A bacterium according to claim 10, wherein the bacterium is of a fast-growing strain of Rhizobium.

14. A bacterium according to claim 10, the bacterium being selected from the group consisting of a Nod+ Fix+ isolate of fast-growing R. japonicum USDA257 (pSym257::191::Tn5-mob) (RP4-4), fast-growing R. japonicum ANU265 (pSym191::Tn5-mob) (RP4-4), fast-growing R. japonicum USDA191-C3 (pSym257::191::Tn5-mob)(RP4-4), and fast-growing R. japonicum USDA191-C3 (Spc$^r$) (pSym191::Tn5-mob)(RP4-4).

15. An inoculant oomposition comprising a carrier material and the bacterium of claim 10.

16. A seed of the genus Glycine coated or otherwise physically associated with material comprising the inoculant composition of claim 15.

17. A method for the production of a Rhizobium bacterium comprising introducing a recombinant DNA molecule of claim 1 containing a Glycine-specific sym gene from a donor Rhizobium strain into a recipient Rhizobium strain selecting for the recipient Rhizobium strain containing the Glycine-specific sym gene and recovering the selected recipient Rhizobium strain.

18. A method according to claim 17, wherein the donor Rhizobium strain is a fast-growing R. japonicum strain.

19. A method according to claim 18, wherein the donor Rhizobium strain is USDA191.

20. A method according to claim 17, wherein the recipient Rhizobium strain is a fast-growing Rhizobium strain.

21. A method according to claim 20, wherein the recipient Rhizobium strain is selected from the group consisting of fast-growing R. japonicum USDA257, fast-growing R. japonicum USDA191 C3, and fast-growing R. japonicum ANU265.

22. The method of claim 17, wherein the introduction of the Glycine-specific sym gene is accomplished by inserting a mob-site flanked with transposon sequences into a pSym of the donor Rhizobium strain by means of a suicide vector;
   introducing transfer genes which mobilize the mob-site flanked with transposon sequences into the donor Rhizobium strain and;
   transferring the pSym containing the mob-site flanked with transposon sequences into the recipient Rhizobium strain by mating with the donor Rhizobium strain.

23. A method according to claim 22, wherein the mob-site is derived from RP4, or a DNA which can mobilize RP4, or a DNA which can be mobilized by RP4.

24. A method according to claim 22, wherein the suicide vector is pSUP5011.

25. A method according to claim 17, wherein the selection comprises the steps of:
   selecting the recipient Rhizobium strain containing the Glycine-specific sym gene by growth on one or more antibiotics;
   selecting the recipient Rhizobium strain containing the Glycine-specific sym gene by identifying and recovering the presumptive recipient Rhizobium strain which symbiotically interact with Glycine root tissue;
   or a combination of the foregoing selection steps.

26. A method according to claim 17, further comprising before introduction of said Glycine-specific sym gene into said recipient Rhizobium strain the step of:
   curing the recipient Rhizobium strain of an endogenous pSym.

27. A method according to claim 17, wherein the recombinant DNA molecule comprising the Glycine-specific sym gene genetically recombines in vivo with an endogenous DNA molecule comprising a replicon, thereby genetically linking the Glycine-specific sym gene with the endogenous replicon.

28. A Rhizobium bacterium capable of Glycine-specific symbiotic nitrogen fixation produced according to the method of claim 17.

29. A bacterium according to claim 28, wherein in the Glycine-specific sym gene is derived from fast-growing Rhizobium japonicum USDA191.

30. A bacterium according to claim 28, which is more competitive than the donor Rhizobium strain.

31. A bacterium according to claim 28, wherein the bacterium is of a fast-growing strain of Rhizobium.

32. A bacterium according to claim 28, the bacterium being selected from the group consisting of a Nod+ Fix+ isolate of fast-growing *R. japonicum* USDA257 (pSym257::191::Tn5-mob)(RP4-4), fast-growing *R. japonicum* ANU265 (pSym191::Tn5-mob) (RP4-4) fast-growing *R. japonicum* USDA191-C3 (pSym257::191::Tn5-mob)(RP4-4), and fast-growing *R. japonicum* USDA191-C3 (Spc$^r$) (pSym191::Tn5-mob(RP4-4).

33. An inoculant composition comprising a carrier material and the bacterium of claim 28.

34. A seed of the genus Glycine coated or otherwise physically associated with the inoculant composition of claim 33.

* * * * *

UNITED STATES PATENT AND TRADEMARK OFFICE
CERTIFICATE OF CORRECTION

PATENT NO. : 4,818,696

DATED : April 4, 1989

Page 1 of 2

INVENTOR(S) : Edward R. Appelbaum, Thomas J. McLoughlin, Michael P. O'Connell

It is certified that error appears in the above-identified patent and that said Letters Patent is hereby corrected as shown below:

At the first column on the first page of the patent under "OTHER PUBLICATIONS" at line 3, please rewrite "Ruukun," as --Ruvkun,--. At the second column on the first page of the patent, at line 8, please rewrite "Pohler," as --Puhler,--. At column 1, line 38, please rewrite "abaerrant," as --aberrant--; At column 1, line 62, please rewrite "Puhluer," as --Puhler,--. At column 2, line 44, please insert --a-- after "containing". At column 3, line 67, please rewrite "sum" as --sym--. At column 4, line 1, please insert --a-- after "particular"; At column 4, line 3, please rewrite "sequesnces" as --sequences--; At column 4, line 6, please rewrite "prefered" as --preferred--; At column 4, line 14, please rewrite "provive" as --provide--; At column 4, line 21, please insert --is-- after "gene"; At column 4, line 63, please insert --which-- after "factor". At column 5, 6th line from the bottom, please rewrite "anumber" as --a number--. At column 6, lines 6 and 7, please rewrite "the three lettered schemes diagram possible outcomes of the manipulations." as --three possible outcomes of the manipulations are shown.--; At column 6, line 12, please insert --as-- after "ambiguities". At column 7, line 34, please delete "such". At column 9, line 12, please rewrite "by" as --be--. At column 10, line 57, please rewrite "designations" as --designation--; At column 10, line 65, please rewrite "spectinomycom" as --spectinomycin--. At column 11, line 16, please rewrite "abberent" as --aberrant--; At column 11, line 27, please rewrite "Agriultural" as --Agricultural--; At column 11, line

UNITED STATES PATENT AND TRADEMARK OFFICE
CERTIFICATE OF CORRECTION

PATENT NO. : 4,818,696

DATED : April 4, 1989

Page 2 of 2

INVENTOR(S) : Edward R. Appelbaum, Thomas J. McLoughlin, Michael P. O'Connell

It is certified that error appears in the above-identified patent and that said Letters Patent is hereby corrected as shown below:

38, please rewrite "leguminosarum." as --leguminosarum,--. At column 13, line ( please rewrite "mob--" as -- mob- --; At column 13, line 31, please rewrite "USDA191-s" as --USDA191's--; At column 13, second line from the bottom, please rewrite "abberant" as --aberrant--. At column 14, lines 2 and 3, please rewrite "abberant" as --aberrant--; At column 14, line 18, please rewrite "abberant" as --aberrant--; At column 14, line 23, please rewrite "abberant" as --aberrant--. At Table 2, lines 12 and 13, at both occurrences, please rewrite "melilati" as --meliloti--. At column 15, claim 3, line 22, please insert --is derived    -- after "mob-site"; At column 15, claim 15, line 67, please rewrite "oomposition" as --composition--. At column 16, claim 17, line 19, please insert --;-- after "strain"; At column 16, claim 25, line 61, please rewrite "interact" as --interacts--; At column 18, claim 32, line 7, please insert --,-- after "(RP4-4)--.

Signed and Sealed this

Second Day of January, 1990

Attest:

JEFFREY M. SAMUELS

Attesting Officer

Acting Commissioner of Patents and Trademarks